US00PP11766P2

(12) United States Plant Patent
Head

(10) Patent No.: US PP11,766 P2
(45) Date of Patent: Feb. 6, 2001

(54) LOROPETALUM PLANT NAMED 'SNOWMOUND'

(75) Inventor: Robert Harold Head, Seneca, SC (US)

(73) Assignee: Head Ornamentals, Inc., Seneca, SC (US)

( * ) Notice: Under 35 U.S.C. 154(b), the term of this patent shall be extended for 0 days.

(21) Appl. No.: 09/292,196

(22) Filed: Apr. 15, 1999

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Loropetalum plant named 'Snowmound', characterized by its compact and procumbent growth habit when young developing a globose mound of descending branches with age; dark green leaves; distinctive leaf shape and texture; short internodes giving a full and dense foliage cover; reddish stipules; self-cleaning flowers; adaptability to many varied environments with respect to soil types and light levels; and hardy to Zones 7A to 9B to Zone 6B (USDA Hardiness Map).

4 Drawing Sheets

BACKGROUND OF THE INVENTION

The present invention relates to a new and distinct cultivar of Loropetalum, botanically known as *Loropetalum chinense* forma *prostratum*, commonly referred to as Chinese Witch Hazel, and hereinafter referred to by the cultivar name 'Snowmound'.

The new Loropetalum is a product of a planned breeding program conducted by the Inventor in Seneca, S.C. The objective of the program is to create and develop new Loropetalum cultivars that are compact and prostrate and suitable as ground-cover plants, with good durable foliage and profuse flowering.

The new Loropetalum originated from a self pollination by the Inventor of an unnamed selection of *Loropetalum chinense*. This unnamed selection was chosen on the basis of its excellent cold hardiness to Zones 7A to 9B to Zone 6B (USDA Hardiness Map). The cultivar 'Snowmound' was discovered and selected by the Inventor as a compact and prostrate plant within the progeny of the stated self pollination in a controlled environment in Seneca, S.C. in 1988.

Plants of the new Loropetalum differ from plants of the parent, the unnamed selection of *Loropetalum chinense*, in the following characteristics:

1. Plants of the new Loropetalum are procumbent in shape when young becoming a globose mound of descending branches with age whereas plants of the parent selection are large shrubs to small trees about 5 meters in height and about 5 meters in diameter with a deliquescent limb growth.
2. Plants of the new Loropetalum and the parent selection differ in leaf color.
3. Leaves of plants if the new Loropetalum are shorter and narrower than leaves of plants of the parent selection.
4. Leaves of plants of the new Loropetalum are revolute and rugulose whereas leaves of plants of the parent selection are smooth.
5. Plants of the new Loropetalum have much shorter internodes than plants of the parent selection.

Asexual reproduction of the new Loropetalum by semi-hardwood or hardwood stem cuttings taken in a controlled environment in Seneca, S.C., has shown that the unique features of this new Loropetalum are stable and reproduced true to type in successive generations.

BRIEF SUMMARY OF THE INVENTION

The new Loropetalum has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Snowmound'. These characteristics in combination distinguish 'Snowmound' as a new and distinct cultivar:

1. Plants of the new Loropetalum are compact and procumbent growth habit when young developing a globose mound of descending branches with age.
2. Plants of the new Loropetalum have a deep dark green leaf color.
3. Plants of the new Loropetalum have a distinctive leaf shape and texture.
4. Plants of the new Loropetalum have short internodes giving a full and dense foliage cover.
5. Plants of the new Loropetalum have reddish stipules.
6. Plants of the new Loropetalum have self-cleaning flowers.
7. Plants of the new Loropetalum are adaptable to many varied environments with respect to soil types and light levels.
8. Plants of the new Loropetalum are hardy to Zones 7A to 9B to Zone 6B (USDA Hardiness Map).

Plants of the new Loropetalum can be compared to plants of the *Loropetalum chinense* cultivar 'Snow Dance', not patented. However, in side-by-side comparisons conducted in Seneca, S.C., plants of the new Loropetalum differ from plants of the 'Snow Dance' in the following characteristics:

1. Plants of the new Loropetalum are procumbent in shape when young becoming a globose mound of descending branches with age whereas plants of the cultivar 'Snow Dance' are shrubby with ascending divaricate limb growth.

2. Plants of the new Loropetalum and the cultivar 'Snow Dance' differ in leaf color.
3. Leaves of plants of the new Loropetalum are shorter and narrower than leaves of plants of 'Snow Dance'.
4. Leaf shape of plants of the new Loropetalum is ovate to obovate with oblique to subequal leaf base and rounded to slightly retuse apex whereas leaf shape of plants of the cultivar 'Snow Dance' is oval to obovate with oblique to equilateral base and subacute apex.
5. Leaves of plants of the new Loropetalum are revolute and rugulose whereas leaves of plants of the cultivar 'Snow Dance' are mostly smooth.
6. Plants of the new Loropetalum have much shorter internodes than plants of the cultivar 'Snow Dance'.
7. Internode stem color of plants of the new Loropetalum is brown whereas internode stem color of the cultivar 'Snow Dance' is tan.
8. Stipules of plants of the new Loropetalum are red in color whereas stipules of plants of the cultivar 'Snow Dance' are green in color.

Plants of the new Loropetalum can be compared to plants of the *Loropetalum chinense* cultivar 'Hillier Form', not patented. However, in side-by-side comparisons conducted in Seneca, S.C., plants of the new Loropetalum differ from plants of the cultivar 'Hillier Form' in the following characteristics:

1. Plants of the new Loropetalum are procumbent in shape when young becoming a globose mound of descending branches with age whereas plants of the cultivar 'Hillier Form' are shrubby with divergent limb growth.
2. Plants of the new Loropetalum and the cultivar 'Hillier Form' differ in leaf color.
3. Leaves of plants of the new Loropetalum are much shorter and narrower than leaves of plants of 'Hillier Form'.
4. Leaf shape of plants of the new Loropetalum is ovate to obovate with oblique to subequal lead base and rounded to slightly retuse apex whereas leaf shape of plants of the cultivar 'Hillier Form' is oval to ovate with oblique to equilateral base and subacute to rounded apex.
5. Leaves of plants of the new Loropetalum are more rugulose than leaves of plants of the cultivar 'Hillier Form'.
6. Plants of the new Loropetalum have shorter internodes than plants of the cultivar 'Hillier Form'.
7. Internode stem color of plants of the new Loropetalum is brown whereas the internode stem color of plants of the cultivar 'Hillier Form' is tan.
8. Stipules of plants of the new Loropetalum are red in color whereas stipules of plants of the cultivar 'Hillier Form' are green in color.

BRIEF DESCRIPTION OF THE PHOTOGRAPHS

The accompanying colored photographs illustrate the overall appearance of the new Loropetalum, showing the colors as true as it is reasonably possible to obtain in colored reproduction of this type.

The photograph on the first sheet comprises a side perspective view of a typical 10-year old plant of 'Snowmound' during the dormant season.

The photograph on the second sheet comprises a side perspective view of typical plants of 'Snowmound'; 10-year old plant (center) in flower and two 2-year old plants in flower (left) and starting new growth (right).

The photograph at the top of the third sheet comprises a close-up view of mature growth at bud break with leaf, stem and flower bud development. The photograph at the bottom of the third sheet comprises a close-up view of adaxial and abaxial surfaces of mature growth at bud break and flower bud development.

The composite photographs on the fourth sheet comprise close-up views of the various aspects of plant stem, flower and leaf development:

FIG. 1. Adaxial surface of previous and current season's growth.

FIG. 2. Abaxial surface of previous and current season's growth.

FIG. 3. Two developing flower buds.

FIG. 4. Two developed flowers.

FIG. 5. Developing terminal cluster of flower buds on lateral branch.

FIG. 6. Two mature flower clusters on stem terminals.

FIG. 7. Adaxial leaf surface of current season's growth.

FIG. 8. Abaxial leaf surface of current season's growth.

FIG. 9. Adaxial leaf surface of previous season's growth.

FIG. 10. Abaxial leaf surface of previous season's growth.

Flower and foliage colors in the photographs may appear different from the actual colors due to light reflectance.

DETAILED BOTANICAL DESCRIPTION

The aforementioned and following observations, measurements, values, and comparisons describe plants grown in Seneca, S.C., under full sun outdoor conditions which closely approximate commercial production conditions. During the winter, plants were exposed to minimum night temperatures of −15° C. and maximum day temperatures of −2° C. During the summer, plants were expose to minimum night temperatures of 5° C. and maximum day temperatures of 40° C.

Plants used for the description were grown in 5-liter black plastic nursery containers and were about 20-months old from a rooted liner. In the following description, color references are made to The Royal Horticultural Society Colour Chart except where general terms of ordinary dictionary significance are used. Numerical values represent averages of six typical plants or specimens.

Botanical classification: *Loropetalum chinense* forma *prostratum* cultivar 'Snowmound'.

Parentage: Self pollination of an unnamed selection of *Loropetalum chinense.*

Propagation:

*Type.*—By stem cuttings. Eight to 10-cm long stem cuttings of previous or current season's growth of firm, semi-hardwood or mature hardwood stems, can be taken in all seasons.

*Time to initiate roots.*—Summer: About 30 days at temperatures of 27 to 30° C. Winter: About 50 days at temperatures of 15.6 to 16.6° C.

*Root description.*—Robust, adapting to many soil environments. Root system develops gradually from callused stem base. Adventitious root tips emerge from epidermis of stem base treated with indolebutyric acid (IBA) preparations. Developed roots are prolific, medium fine, fibrous, well-branched and vigorous.

Plant description:

*Plant form.*—Dwarf, creeping, freely branching evergreen shrub; procumbent when young and globose mound with descending limbs with age.

*Growth habit.*—Moderate growth and vigorous. Compact in plant height with short internodes.

*Plant size.*—Ten-year old plants are about 38 cm in height and about 180 cm in width. Annual growth rate is about 8 to 15 cm of radial growth and about 3 to 4 cm of vertical growth per year.

*Branching.*—Rapid; branchlets, compressed and decumbent of 3 to 9 cm length. Lateral branch diameter is about 0.75 to 2.5 mm and stem internode length is about 4 to 11 mm.

*Stem description.*—Texture: Dense short stellate hairs of greyed red, 182A. Color: Mature new growth is brown, 200C.

*Leaf description.*—Arrangement: Simple, alternate in a distichous pattern along the stem. Quantity of leaves per lateral branch: About 3 to 20. Shape: Ovate to obovate. Length: About 1.59 cm. Width: About 1.35 cm. Apex: Rounded to slightly retuse; rarely acute. Base: Oblique to subequal. Margin: Entire, revolute. Texture: Adaxial: Coriaceous rugulose, sparsely pubescent with stellate hairs; lustrous sheen. Abaxial: Coriaceous, sparsely pubescent with stellate hairs. Color: Young foliage, adaxial: 139A. Young foliage, abaxial: 191B. Mature foliage, adaxial: 131A. Mature foliage, abaxial: 148B. Petiole length: About 3 to 5 mm. Petiole diameter: About 0.7 to 1.2 mm. Petiole shape: Terete. Petiole color: 137C. Venation pattern: Midvein and four pairs of primary veins conspicuous on adaxial surface; abaxial surface, prominent. Venation color: Adaxial, 131A; abaxial, 148B. Durability of foliage: Exceptionally durable. Stipule length: About 2.5 to 3 mm. Stipule color: About 181A.

*Flower description.*—Flowering habit: Globose heads on terminals. Natural flowering season: In the spring, plants will form flowers on terminals of new growth developing from axillary buds and terminal buds after sufficient chilling hours during dormant season. Quantity of flowers: Four to eight flowers in globose heads on branchlet terminals abundantly cover the plant as a result of compact plant habit and closely-spaced internodes. Flowers: Shape: Four to five strap-like petals forming a loose funnel. Diameter: About 2.5 to 3.5 mm. Height: About 2.5 cm. Quantity of flower buds per lateral stem: Four to fifteen. Longevity on plant: About four to five days. Fragrance: Slight. Flower buds: Shape: Orbicular. Length: About 3 to 3.5 mm. Diameter: About 2.5 to 3.5 mm. Rate of opening: About 5 to 7 days. Color: 155C. Petals: Arrangement: Four to five arising from calyx tube at sepal base. Shape: Linear crinkled strap-like with lacerate to dentate apex and entire margin. Length: About 2 cm. Width: About 2.5 to 2.8 mm. Texture: Smooth, glaborous. Color: When opening and fully opened: Both surfaces, 155A; fading to 155B. Sepals: Arrangement: Opposite; four per flower. Calyx erect and cruciform. Shape: Ovate with rounded to slight pointed apex and entire revolute margin. Length: About 2.5 to 3 mm. Width: About 2 to 2.5 mm. Texture: Crinkled. Color, both surfaces: 145B. Peduncles: Shape: Terete. Aspect: Horizontal to slightly erect to stem axis. Length: About 3 to 4 mm. Diameter: About 1 to 1.5 mm. Texture: Yellowish stellate pubescent. Color: 145B. Reproductive organs: Stamens: Four. Pistils: Two.

Disease resistance: No diseases common to Loropetalum have been observed under commercial greenhouse conditions.

Seed/fruit production:

*Fruit.*—Quantity: None to two; On older plants, more than 15 years old, about 400 fruits per plant have been observed; with about one to six fruits per lateral branch. Length: About 8.6 mm. Diameter: About 6.7 mm. Color: 146A. Texture: Woody, scabrous.

*Seed.*—Quantity: One to two seeds per fruit. Length: About 5.4 mm. Diameter: About 3 mm. Color: 200A. Days from flowering to dehiscence: About 190.

Hardiness: Plants of the new Loropetalum are very hardy to Zones 7A to 9B to Zone 6B (USDA Hardiness Map).

It is claimed:

1. A new and distinct Loropetalum plant named 'Snowmound', as illustrated and described.

* * * * *

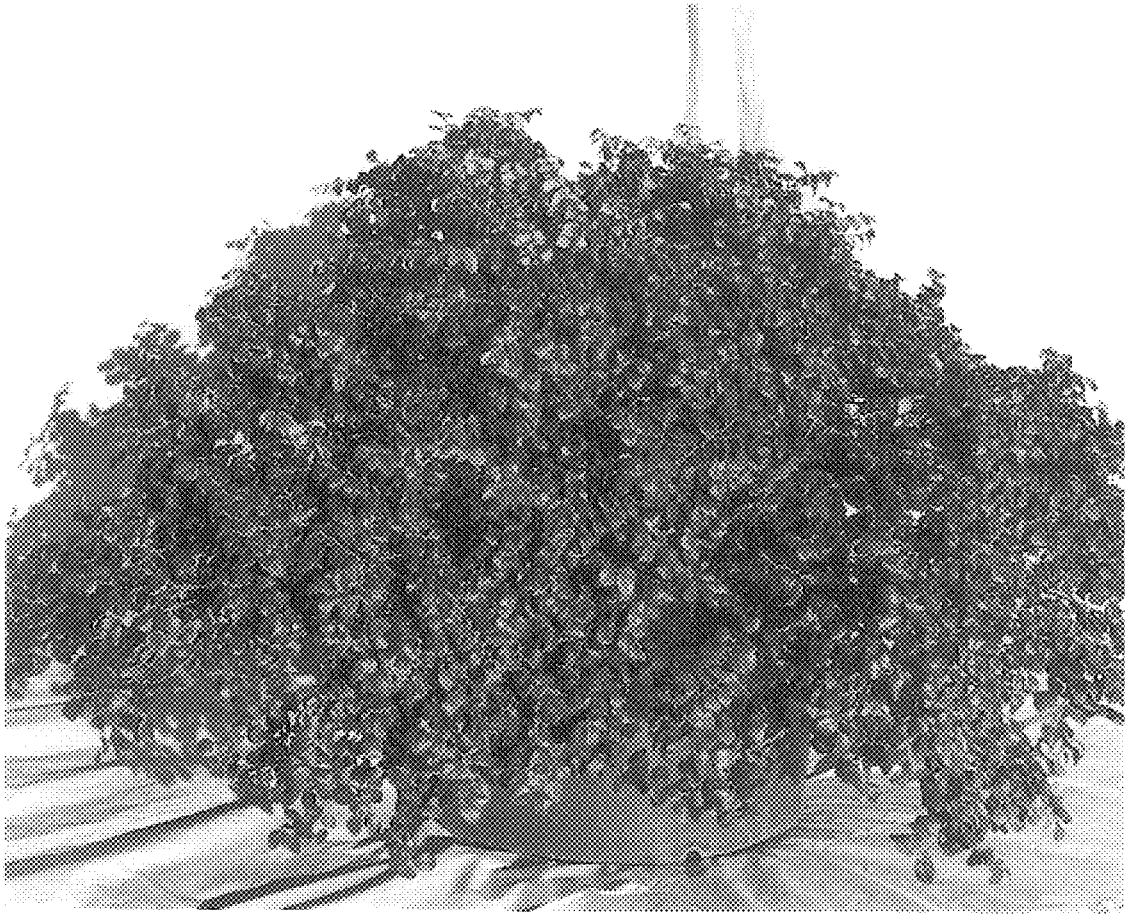

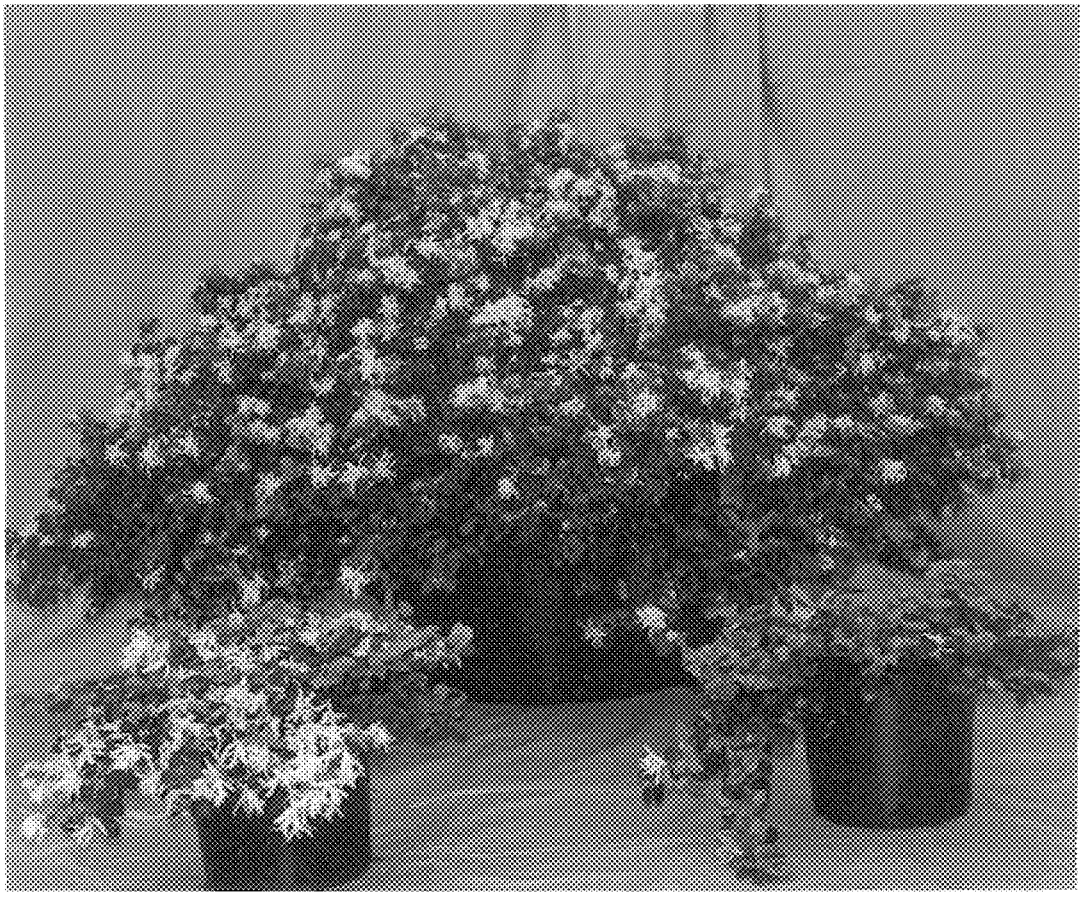

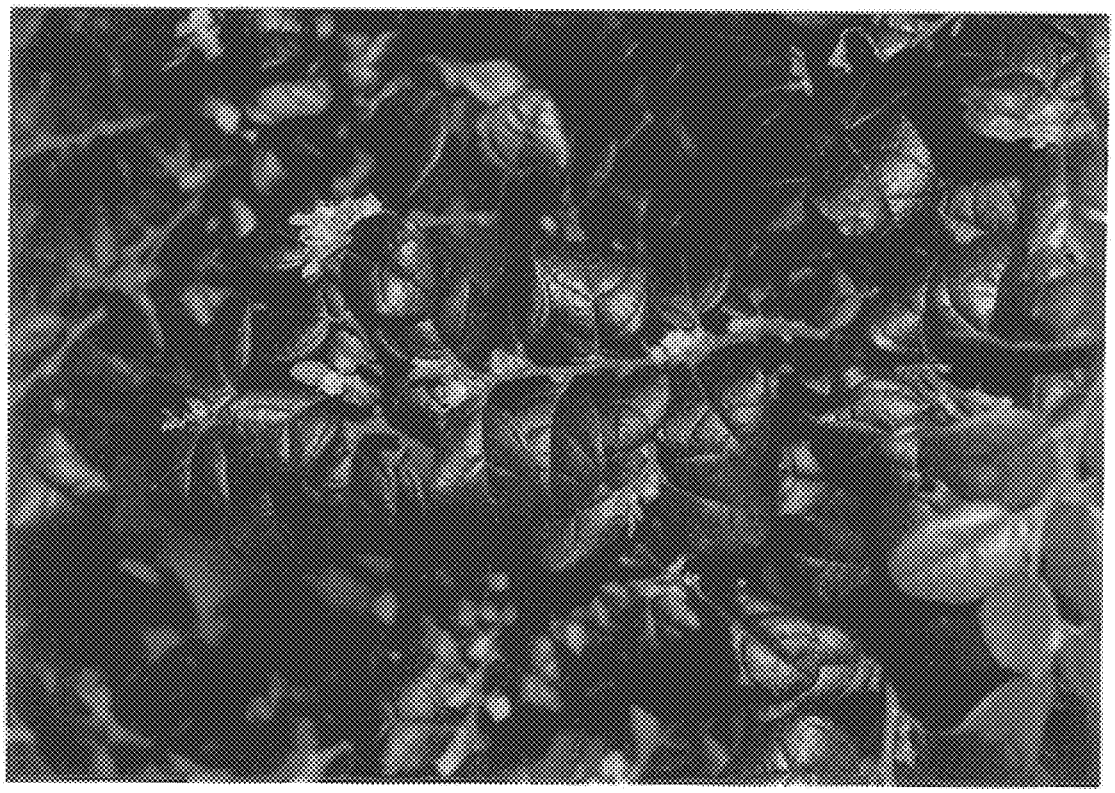
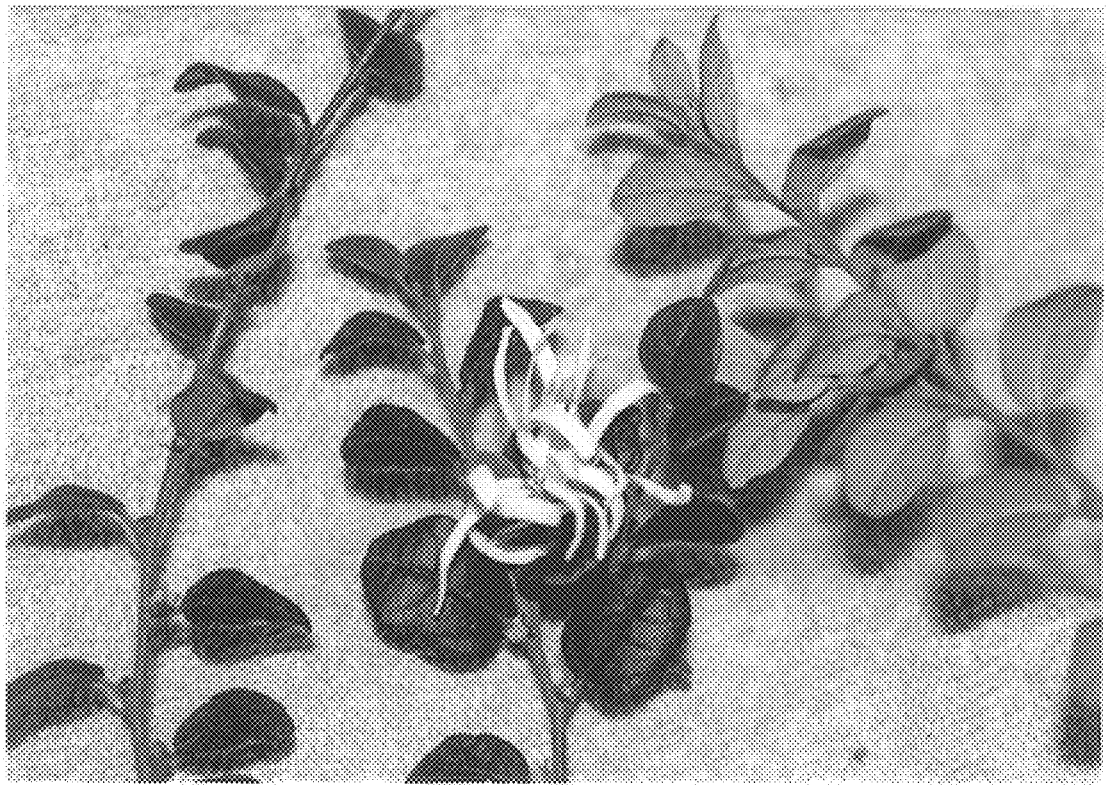

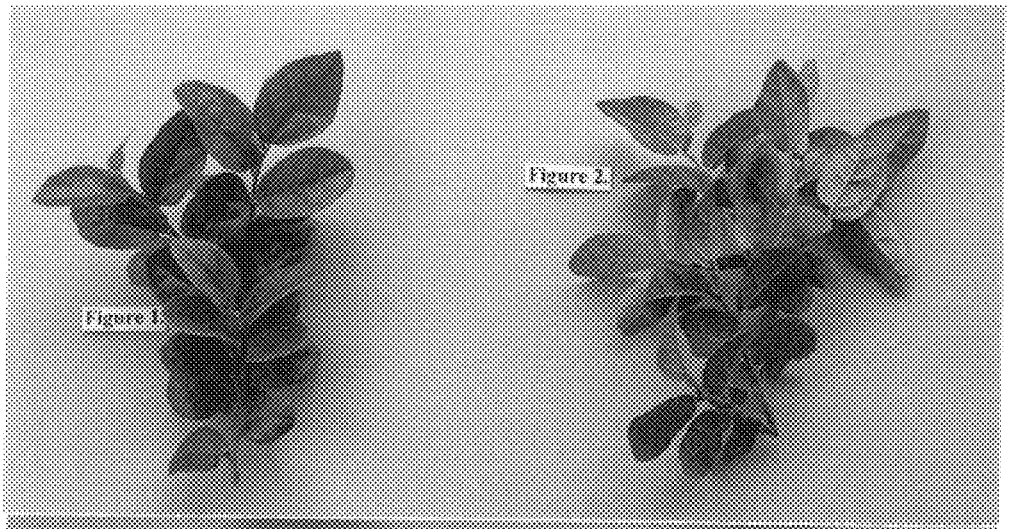
Figure 1.
Figure 2.
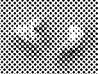
Figure 3.
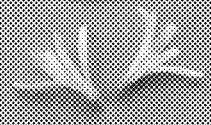
Figure 4.
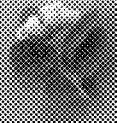
Figure 5.
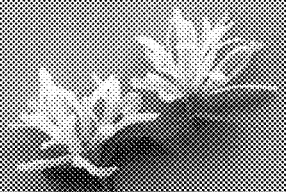
Figure 6.
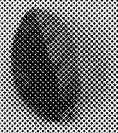
Figure 7.
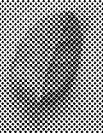
Figure 8.
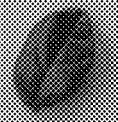
Figure 9.
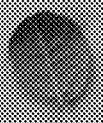
Figure 10.